US00PP27945P2

(12) United States Plant Patent
Hartman

(10) Patent No.: US PP27,945 P2
(45) Date of Patent: Apr. 25, 2017

(54) ***CALADIUM* PLANT NAMED 'POSY PINK'**

(50) Latin Name: *Caladium×hortulanum*
Varietal Denomination: Posy Pink

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,538

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'Posy Pink', characterized by its intermediate height, upright and uniformly mounded plant habit; moderately vigorous growth habit and rapid growth rate; fancy type leaves that have reddish pink-colored veins with pink-colored areas surrounding the venation, dark green-colored margins and interveinal areas that are suffused with dark red, grey green and green; and above average tolerance to *Xanthomonas* Leaf Spot.

4 Drawing Sheets

Botanical designation: *Caladium×hortulanum.*
Cultivar denomination: 'POSY PINK'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Posy Pink'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2007 in Avon Park, Fla. of *Caladium×hortulanum* 'Aaron', not patented, as the female, or seed, parent with *Caladium×hortulanum* 'John Peed', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2009 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Posy Pink'. These characteristics in combination distinguish 'Posy Pink' as a new and distinct *Caladium* plant:

1. Intermediate in height, upright and uniformly mounded plant habit.
2. Moderately vigorous growth habit and rapid growth rate.
3. Fancy type leaves that have reddish pink-colored veins with pink-colored areas surrounding the venation, dark green-colored margins and interveinal areas that are suffused with dark red, grey green and green.
4. Above average tolerance to *Xanthomonas* Leaf Spot.

Plants of the new *Caladium* differ primarily from plants of the female parent, 'Aaron', in the following characteristics:

1. Plants of the new *Caladium* and 'Aaron' differ in leaf color as leaves of 'Aaron' have white-colored venation and radiating interveinal areas surrounded with green-colored borders.
2. Plants of the new *Caladium* and 'Aaron' differ in leaf petiole color as leaf petioles of 'Aaron' are green in color.
3. Plants of the new *Caladium* and 'Aaron' differ in tolerance to *Xanthomonas* Leaf Spot as plants of 'Aaron' are more susceptible to damage resulting from *Xanthomonas* Leaf Spot than plants of the new *Caladium.*

Plants of the new *Caladium* differ primarily from plants of the male parent, 'John Peed', in the following characteristics:

1. Plants of the new *Caladium* and 'John Peed' differ in leaf color as leaves of 'John Peed' have dark red-colored centers and red-colored venation with dark green-colored margins.

2. Plants of the new *Caladium* and 'John Peed' differ in leaf petiole color as leaf petioles of 'John Peed' are dark pink with dark green to close to black-colored stippling and streaks.

Plants of the new *Caladium* can be compared to plants of *Caladium×hortulanum* 'Rose Glow', disclosed in U.S. Plant Pat. No. 20,070. In side-by-side comparisons, plants of the new *Caladium* differ primarily from plants of 'Rose Glow' in the following characteristics:

1. Plants of the new *Caladium* and 'Rose Glow' differ in leaf color as leaves of 'Rose Glow' are red purple in color with white-colored midveins, green-colored borders and dark green-colored margins.
2. Plants of the new *Caladium* and 'Rose Glow' differ in leaf petiole color as leaf petioles of 'Rose Glow' are tan green in color with darker green-colored tessellations and speckles.
3. Plants of the new *Caladium* and 'Rose Glow' differ in tolerance to *Pythium* Root Rot as plants of 'Rose Glow' are more susceptible to damage resulting from *Pythium* Root Rot than plants of the new *Caladium*.

Plants of the new *Caladium* can be compared to plants of *Caladium×hortulanum* 'Carolyn Whorton', not patented. In side-by-side comparisons, plants of the new *Caladium* differ primarily from plants of 'Carolyn Whorton' in the following characteristics:

1. Plants of the new *Caladium* and 'Carolyn Whorton' differ in leaf color as leaves of 'Carolyn Whorton' are olive green in color with pink-colored blotches and bright red to rose pink-colored venation.
2. Plants of the new *Caladium* and 'Carolyn Whorton' differ in leaf petiole color as leaf petioles of 'Carolyn Whorton' are tan pink in color with darker-colored stippling.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Posy Pink' in a container and grown in a shadehouse (tuber not de-eyed).

The photograph at the top of the second sheet is a comparison view of typical potted plants of the female parent, 'Aaron' (right), 'Posy Pink' (center) and the male parent, 'John Peed' (left).

The photograph at the bottom of the second sheet is a comparison view of typical potted plants of 'Rose Glow' (right), 'Posy Pink' (center) and 'Carolyn Whorton' (left).

The photograph at the top of the third sheet is a comparison view of typical plants of 'Posy Pink' grown in containers; the plant on the left has not had its tuber de-eyed and the plant on the right has had its tuber de-eyed prior to planting.

The photograph at the bottom of the third sheet is a side perspective view of typical plants of 'Posy Pink' grown in an open field.

The photograph at the top of the fourth sheet is a close-up view of typical freshly-harvested tubers and roots of 'Posy Pink'.

The photograph at the bottom of the fourth sheet is a close-up view of typical inflorescences of 'Posy Pink'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were ten weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Posy Pink'.

Parentage:

*Female, or seed, parent.*—*Caladium×hortulanum* 'Aaron', not patented.

*Male, or pollen, parent.*—*Caladium×hortulanum* 'John Peed', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description (outdoor nursery-grown plants).*—Appearance: Multi-segmented and somewhat flattened; individual segments elliptic to ovate. Height: About 3.9 cm. Diameter: About 4.4 cm to 4.9 cm. Segment height: About 2 cm. Segment diameter: About 1.7 cm to 2 cm. Axillary buds, height: About 5 mm to 6 mm. Texture: Thick, starchy; somewhat brittle. Color: Epidermis, freshly-harvested: Close to 159D; outer skin, close to 199A to 199B. Epidermis, dried: Close to 200A. Cortical tissue: Close to 4C. Axillary buds: Close to 36B. Root description: Thick, fleshy contractile roots; color, close to 155C. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Intermediate in height, upright and uniformly mounded plant habit; moderately vigorous and dense growth habit; rapid growth rate; potted plants in finished or saleable form in about eight weeks after planting tubers; leaf petioles and leaves arise from one or more growing points on tubers; petioles mostly upright and outwardly leaning with development.

*Plant height, from soil level to top of foliar plane, shadehouse-grown potted plants*.—About 27 cm to 30 cm.

*Plant height, from soil level to top of inflorescences, shadehouse-grown potted plants*.—About 36 cm.

*Plant diameter or spread, shadehouse-grown potted plants*.—About 37 cm to 43 cm.

*Number of shoots per plant, shadehouse-grown potted plants, tubers not de-eyed*.—About one to two develop per #1 tuber.

*Number of shoots per plant, shadehouse-grown potted plants, tubers de-eyed*.—About three develop per #1 tuber.

*Cataphylls, shadehouse-grown potted plants*.—Length: About 4.9 cm to 8.5 cm. Width: About 1.3 cm to 1.6 cm. Shape: Wedge-shaped. Apex: Acute. Base: Sheathing the stem. Color, inner surface: Close to N155C; colors and patterns on the outer surface are visible on the inner surface. Color, outer surface: Close to 199D and close to 159C tinged with close to 147C; variably streaked and stippled with close to 200A tinged with close to 147A; with development, color becoming closer to 200B to 200C.

Leaf description:

*Arrangement and type*.—Alternate; simple; fancy-type.

*Length, shadehouse-grown potted plants*.—About 19 cm to 27 cm.

*Width, shadehouse-grown potted plants*.—About 14 cm to 21 cm.

*Shape*.—Broadly ovate.

*Apex*.—Acuminate to acute.

*Base*.—Sagittate to peltate.

*Margin*.—Entire; mostly flat with broad undulations.

*Texture, upper and lower surfaces*.—Smooth, glabrous; somewhat rigid and slightly rugose.

*Luster, upper surface*.—Dull sheen.

*Luster, lower surface*.—Glaucous, dull sheen.

*Venation pattern*.—Pinnate.

*Color, shadehouse-grown potted plants*.—Developing and fully expanded leaves, upper surface: Midvein: Close to 60A. Primary veins: Close to 59A and 187B. Areas surrounding venation: Close to 53B to 53C tinged with close to 184C. Interveinal areas: Suffusion of close to 183A, 185B, 185C, 49D and 147A. Margins: Towards the margins, close to 147A tinged with close to 137A; thin margin, close to 187A. Basal notch: Close to 187A. Developing and fully expanded leaves, lower surface: Midvein: Close to 182D streaked and mottled with close to 185B. Primary veins: Close to 195A sparsely streaked with close to 184B. Areas surrounding venation: Close to 184C. Interveinal areas: Close to 183C to 183D, close to 191A and/or close to 191A tinged with close to 189A. Margins: Thin margin, close to 187B. Basal notch: Close to 187B.

*Petioles*.—Aspect: Initially upright and straight; with development, leaning outwardly; flexible. Length, shadehouse-grown potted plants: About 20 cm to 23 cm. Diameter, distally, shadehouse-grown potted plants: About 4.5 mm to 6 mm. Diameter, proximally, shadehouse-grown potted plants: About 8mm to 11 mm. Texture: Smooth, glabrous; glaucous. Color, shadehouse-grown potted plants: Close to 200A, 202A or N170D flushed or densely streaked and stippled with close to 200A; below the leaf and petiole junction, close to 182A flushed or tinged with close to 200A to 200B. Wing length, shadehouse-grown potted plants: About 5.5 cm to 7.2 cm. Wing diameter, shadehouse-grown potted plants: About 8 mm. Texture, inner and outer surfaces: Smooth, glabrous. Luster, inner and outer surfaces: Dull sheen. Wing color, shadehouse-grown potted plants: Inner surface: Close to N155C; colors and patterns on the outer surface are visible on the inner surface. Outer surface: Close to 199D and close to 159C tinged with close to 147C to 147D; densely and variably streaked, stippled or mottled with close to 200A tinged with close to 147B.

Inflorescence description: Inflorescences observed on ten week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring and summer in central Florida; flowers develop about ten weeks after growth commences; inflorescences last about three days before fading; inflorescences persistent.

*Spathe*.—Length, overall: About 13.5 cm. Length, distal open portion: About 9 cm. Length, proximal closed portion: About 4.5 cm. Width, distal open portion: About 3.8 cm. Depth, distal open portion: About 2.7 cm. Width, at constriction: About 1.3 cm. Width, proximal closed portion: About 2.1 cm. Shape: Obovate. Apex: Acute. Base: Acute. Margin: Entire. Texture, front and rear surfaces: Smooth, glabrous. Luster, front surface: Dull sheen. Luster, rear surface: Glaucous, dull sheen. Color, front surface: Distal open portion: Close to 155C; towards the margins, close to 192D; with development, color becoming closer to 199B and 200C. Proximal closed portion: Close to 194B to 194C; distally, sparsely streaked with close to 187A; color does not change with development. Color, rear surface: Distal open portion: Close to 157D, 155C and 145D; color does not change with development. Proximal closed portion: Close to 147B and 147C; areas streaked with close to 194B and 194C; color does not change with development.

*Spadix*.—Length, overall: About 8.4 cm. Length, male flower zone: About 4.9 cm. Length, sterile zone: About 1.8 cm. Length, female flower zone: About 1.7 cm. Diameter, male flower zone: About 1 cm. Diameter, sterile flower zone: About 7 mm. Diameter, female flower zone: About 9 mm. Shape: Spindle-shaped. Apex: Acute. Base: Obtuse. Aspect: Upright. Color, mature, male zone: Close to 155D. Color, mature, sterile zone: Close to 155D. Color, mature, female zone: Close to 155A and 159C. Male flowers: Quantity per spadix: About 210. Shape: Obovate. Height: About 3 mm. Diameter: About 3 mm. Pollen amount: Moderate. Pollen color: Close to 4D. Female flowers: Quantity per spadix: About 84. Shape: Obovate. Height: About 3 mm. Diameter: About 1.5 mm. Stigma color: Close to 155A. Ovary color: Close to 159C.

*Scape*.—Length: About 22.5 cm. Diameter: About 6.5 mm. Strength: Sturdy; flexible. Aspect: Mostly erect. Texture: Smooth, glabrous. Luster: Dull sheen; glaucous. Color: Close to 147B tinged with close to 200C and stippled and streaked with close to 200B; just below spathe, close to 147B stippled and streaked with close to 200B and 200C.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Posy Pink' as illustrated and described.

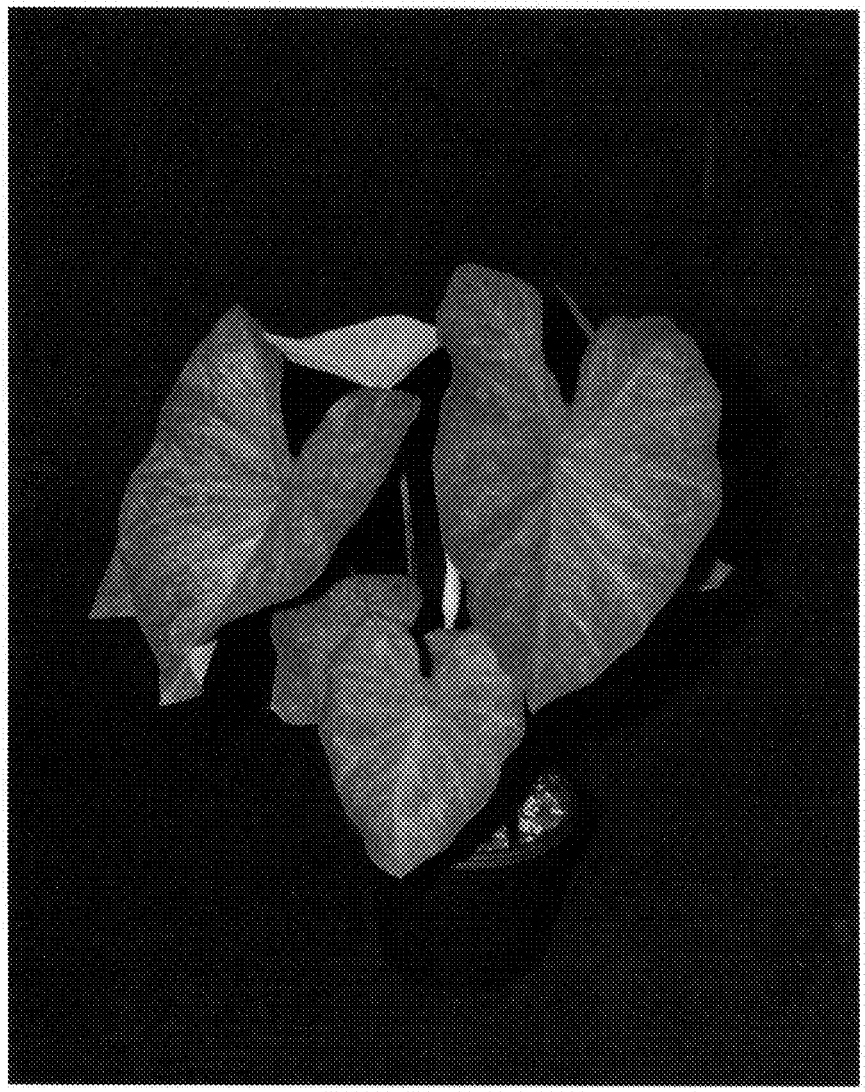

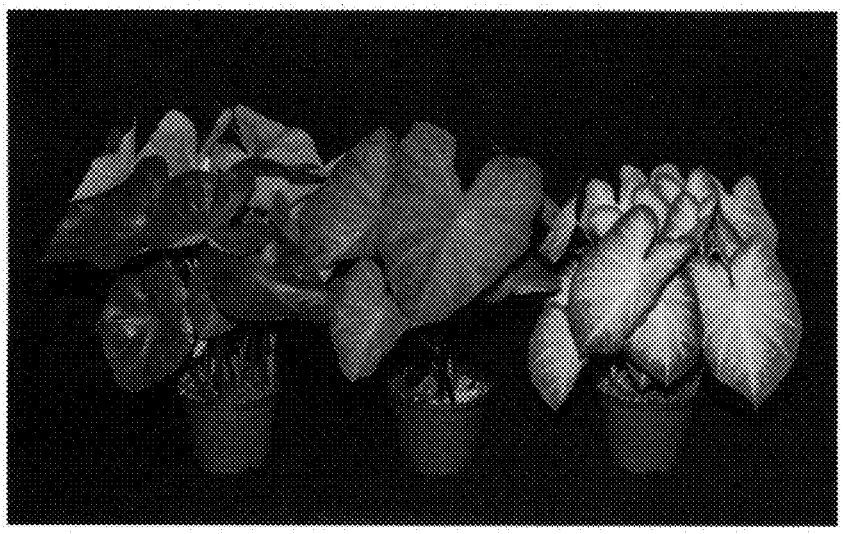
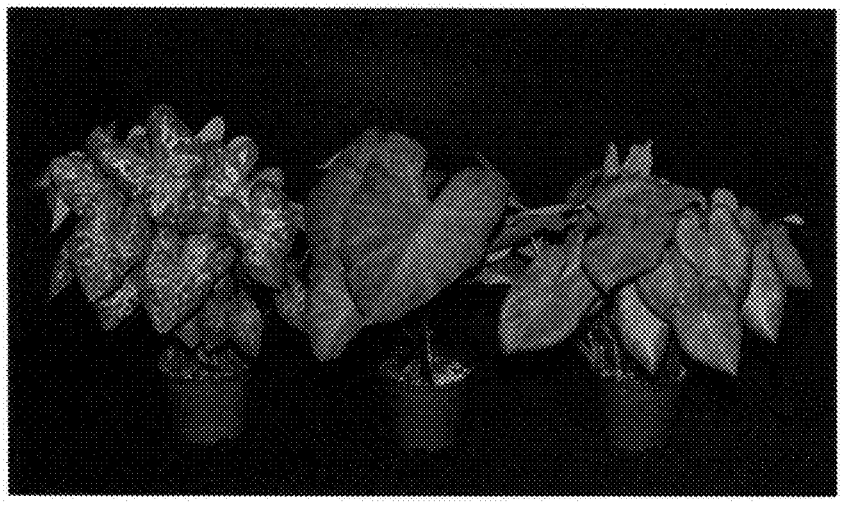

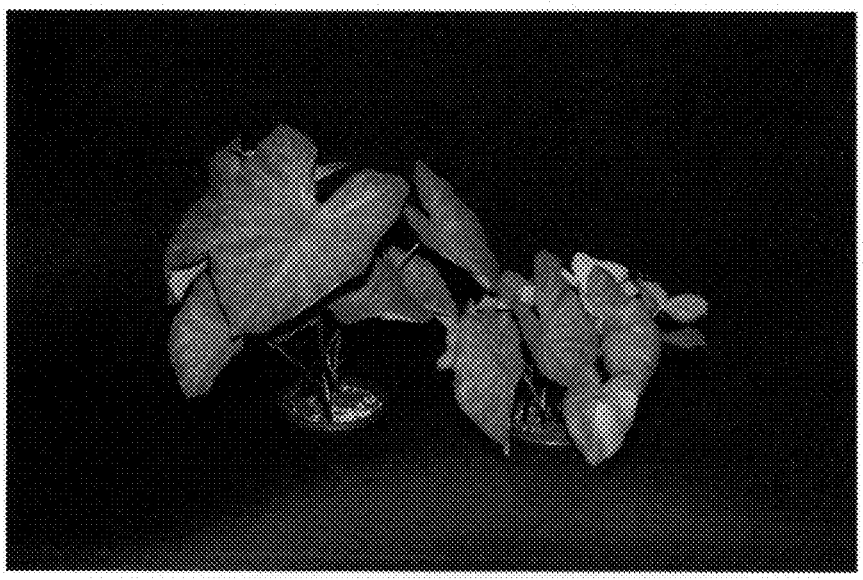
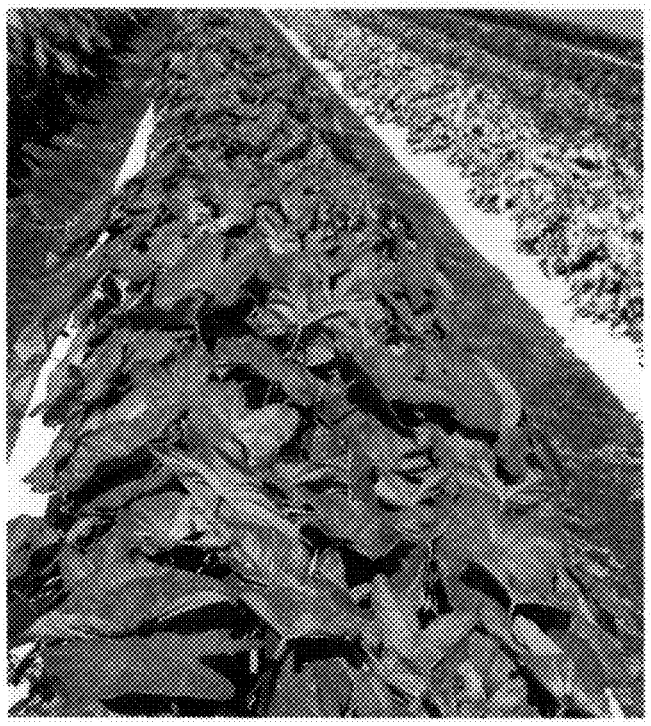

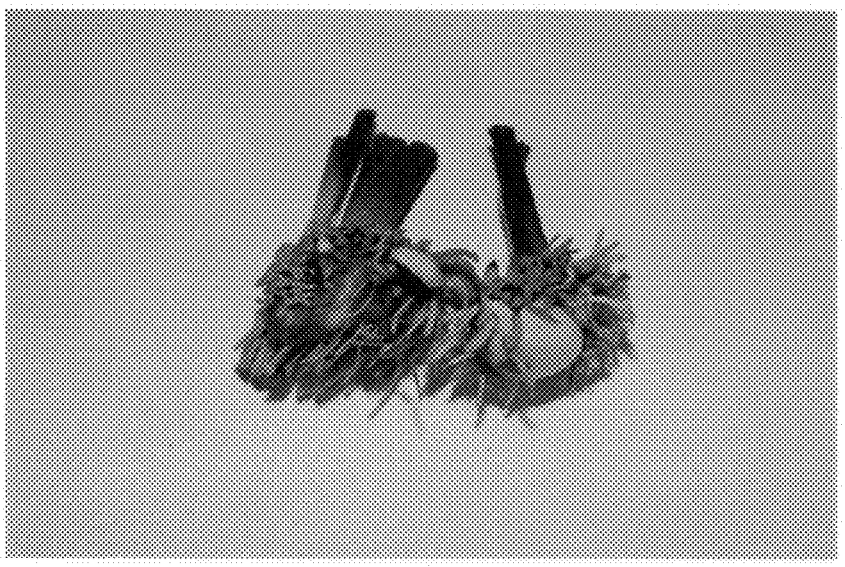
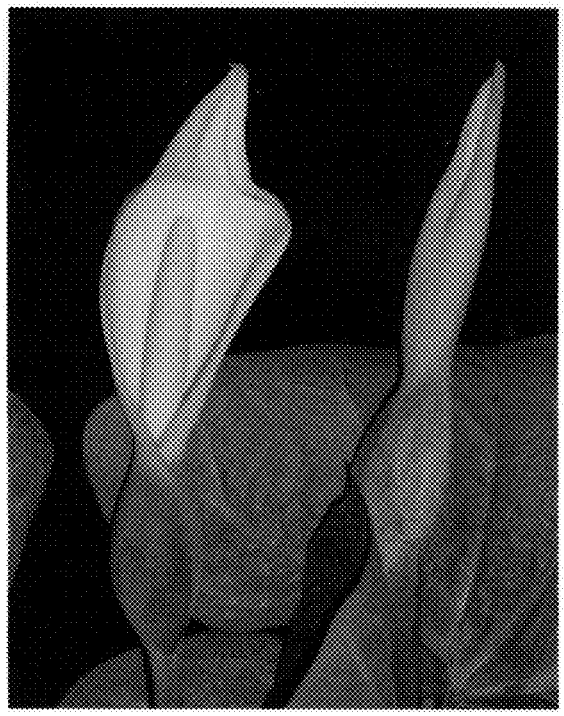

* * * * *